May 6, 1969 E. S. BOERNER Plant Pat. 2,885
ROSE PLANT
Filed Sept. 14, 1967
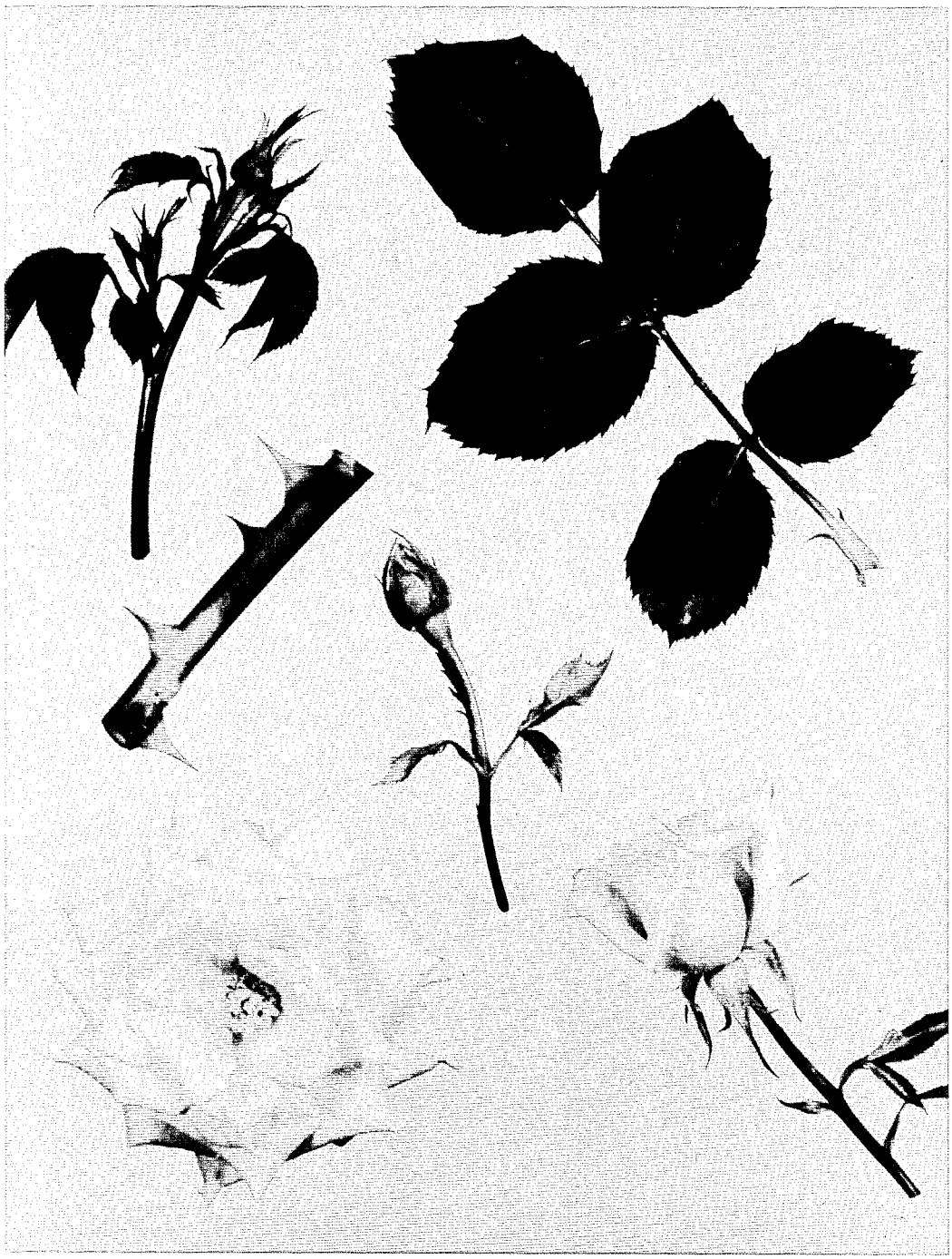
Inventor.
E. S. Boerner, Deceased
By: Lincoln Rochester Trust Company
By: Edward L. Jenner, Trust Officer
and Roger L. Boerner, Executors
By: Robb & Robb, Attorneys.

United States Patent Office

Plant Pat. 2,885
Patented May 6, 1969

2,885
ROSE PLANT

Eugene S. Boerner, deceased, late of Benton, N.Y., by Lincoln Rochester Trust Company, Rochester, N.Y., and Roger L. Boerner, Milwaukee, Wis., executors, assignors to Jackson & Perkins Company, Newark, N.Y., a corporation of New York

Filed Sept. 14, 1967, Ser. No. 667,869
Int. Cl. A01h *5/02*
U.S. Cl. Plt.—26 1 Claim

The present invention relates to a new and distinct variety of rose plant of the floribunda class, which was originated by the late Eugene S. Boerner, deceased, by crossing the rose variety known as "Ginger" (Plant Patent No. 2,293) with an unnamed and unpatented seedling derived from a cross of the variety known as "Ma Perkins" (Plant Patent No. 1,143) × the variety known as "Garnette Supreme" (Plant Patent No. 1,318).

The primary objective of this breeding was to produce a new and improved rose variety having a compact and well-formed plant habit and which is free blooming and useful in all areas. This objective was fully achieved, along with other desirable features, as evidenced by the following unique combination of characteristics which are outstanding in the new variety and which distinguish it from its parents, as well as from all other varieties:

(1) A compact and well-formed plant habit;
(2) Excellent continuity of bloom;
(3) A distinctive and attractive bloom form; and
(4) A distinctive and attractive general color tonality of the flowers corresponding to Thulite Pink, lightly overcast with Cameo Pink Asexual reproduction of the new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature:

Parentage: Seedling.
*Seed parent.*—"Ginger."
*Pollen parent.*—An unnamed seedling of "Ma Perkins" × "Garnette Supreme."

Classification:
*Botanic.*—Floribunda.
*Commercial.*—Floribunda.

*Flower*

(Observations made from specimens grown in a greenhouse at Newark, N.Y., during the forepart of the month of May.)

Blooming habit: Recurrent—continuous.

Bud:
*Size.*—Medium.
*Form.*—Ovoid; is not affected by wet or hot weather.
*Color.*—When sepals first divide—Spinel Red, Plate 26. When petals begin to unfurl—Deep Rose Pink, Plate 12, with the lower half of petal overcast with Rose Color, Plate 12. When half-blown: inside of petals—Thulite Pink, Plate 26, very lightly overcast with Spinel Red, Plate 26; reverse of petals—Deep Rose Pink, Plate 12, lightly overcast with Thulite Pink, Plate 26.
*Sepals.*—Branched; curl back when petals begin to unfurl. Color: inside—Yellowish Glaucous, Plate 41; outside—Light Bice Green, Plate 17.
*Calyx.*—Color—Light Bice Green, Plate 17. Shape—pear. Size—small. Aspect—smooth. Odor when rubbed—none.
*Peduncle.* — Length — long. Aspect — smooth. Strength—erect; heavy. Color—Cress Green, Plate 31.
*Opening.*—Opens up well; is not affected by adverse weather conditions.

Bloom:
*Size.*—Medium. Average size when fully expanded—4 inches.
*Borne.*—Both singly and in irregular clusters; continuously in bloom.
*Stems.*—Medium length; strong.
*Form (when first open).*—High-centered. Permanence—retains its form to the end, with petals becoming slightly quilled.
*Petalage.*—Double (full but open center). Number of petals under normal conditions—from 35 to 40.
*Color.*—Center of flower—Thulite Pink, Plate 26, with lower half of the petal very lightly overcast with Deep Rose Pink, Plate 12. Outer petals—Rosolane Pink, Plate 26, with lower half of the petal lightly overcast with Thulite Pink, Plate 26. Base of petals (aiglet)—white, Plate 53, with center of aiglet overcast with Marguerite Yellow, Plate 30. Inside of petals—Thulite Pink, Plate 26, lightly overcast with Cameo Pink, Plate 26. Reverse of petals—Rose Pink, Plate 12, with lower half of the petal lightly overcast with Spinel Pink, Plate 26. General tonality from a distance—Thulite Pink, Plate 26, lightly overcast with Cameo Pink, Plate 26.
*Discoloration.*—General tonality at end of first day—Thulite Pink, Plate 26, lightly overcast with Cameo Pink, Plate 26. Second day—Thulite Pink, Plate 26, lightly overcast with Cameo Pink, Plate 26. Third day—Thulite Pink, Plate 26, overcast with Cameo Pink, Plate 26.

Petals:
*Texture.*—Thick.
*Appearance.*—Inside—satiny. Outside—shiny.
*Form.*—Oval; slightly notched.
*Arrangement.*—Imbricated (regularly arranged shingle-like).
*Petaloids in center.*—Few; small.
*Persistence.*—Drop off cleanly.
*Fragrance.*—Slight. Nature—tea (average hybrid tea scent).
*Lasting quality.*—On the plant—long. As cut flower—long.

*Reproductive organs*

Stamens, anthers: Small; many; regularly arranged around styles. Color—Mustard Yellow, Plate 16.
Stamens, filaments (threads): Medium length. Color—Thulite Pink, Plate 26.
Pollen: Color—Cream Color, Plate 16.
Styles: Bunched; uneven length; medium length; thin.
Stigmas: Color—Barium Yellow, Plate 16.
Ovaries: All enclosed in calyx.
Hips: None.
Seeds: None.

*Plant*

Form: Bush.
Growth: Vigorous; upright; compact.
Foliage: Compound of 3–7 leaflets.
*Size.*—Medium.
*Quantity.*—Abundant.
*Color.*—New foliage: upper side—Mahogany Red, Plate 2; under side—Hydrangea Red, Plate 27. Old foliage: upper side—Antique Green, Plate 6; under side—Grass Green, Plate 6.

*Shape.*—Oval pointed.

*Texture.*—Upper side—glossy. Under side—smooth,

*Ribs and veins.*—Ordinary.

*Edge.*—Serrated (saw-toothed).

*Serration.*—Both double and single; small.

*Leaf stem.*—Color—Rainette Green, Plate 31. Under side—prickly.

*Stipules.*—Medium length; smooth.

Wood:

*New wood*—Color—Courge Green, Plate 17. Bark—smooth.

*Old wood.*—Color—Bice Green, Plate 17. Bark—smooth.

Thorns:

*Thorns.*—Quantity: on main stalks from base—ordinary; on laterals from stalk—ordinary. Form—narrow base; short; some hooked downward and some hooked upward. Color (when young)—Eugenia Red, Plate 13. Position—irregular.

*Prickles.*—Quantity: on main stalks—none; on laterals—none.

*Short needles.*—Quantity: on main stalks—none; on laterals—none.

What is claimed is:

1. A new and distinct variety of rose plant of the floribunda class, substantially as herein shown and described, characterized particularly as to novelty by the unique combination of a compact and well-formed plant habit, excellent continuity of bloom, a distinctive and attractive bloom form, and a distinctive and attractive general color tonality of the flowers corresponding to Thulite Pink, lightly overcast with Cameo Pink.

No references cited.

ROBERT E. BAGWILL, *Primary Examiner.*